United States Patent
Khalaj et al.

(10) Patent No.: US 11,638,805 B2
(45) Date of Patent: May 2, 2023

(54) MULTI-HEADED CATHETER FOR FLUID DELIVERY

(71) Applicant: Avent, Inc., Alpharetta, GA (US)

(72) Inventors: Steve S. Khalaj, Laguna Hills, CA (US); Eric A. Schepis, Alpharetta, GA (US); Thomas D. Mina, Newport Beach, CA (US)

(73) Assignee: Avent, Inc., Alpharetta, GA (US)

( * ) Notice: Subject to any disclaimer, the term of this patent is extended or adjusted under 35 U.S.C. 154(b) by 426 days.

(21) Appl. No.: 16/286,755

(22) Filed: Feb. 27, 2019

(65) Prior Publication Data
US 2020/0269018 A1    Aug. 27, 2020

(51) Int. Cl.
*A61M 25/00*    (2006.01)
*A61M 31/00*    (2006.01)
(Continued)

(52) U.S. Cl.
CPC ...... *A61M 25/0082* (2013.01); *A61M 3/0254* (2013.01); *A61M 19/00* (2013.01); *A61M 25/007* (2013.01); *A61M 25/0074* (2013.01); *A61M 25/0097* (2013.01); *A61M 25/0662* (2013.01); *A61M 2025/0006* (2013.01);
(Continued)

(58) Field of Classification Search
CPC ...... A61M 2025/0004; A61M 25/0069; A61M 25/007; A61M 25/0071; A61M 2025/018; A61M 1/3653; A61M 1/3659; A61M 1/3661; A61M 19/00; A61M 25/0668; A61M 2025/0025; A61M 25/0028; A61M 25/0029; A61M 25/003
See application file for complete search history.

(56) References Cited

U.S. PATENT DOCUMENTS 5,807,311 A * 9/1998 Palestrant ........... A61M 25/003
604/537
5,957,879 A * 9/1999 Roberts ............... A61M 1/3667
128/898

(Continued)

FOREIGN PATENT DOCUMENTS

EP    2 680 920 B1    1/2014
WO    WO 02/07810 A2    1/2002

OTHER PUBLICATIONS

International Search Report and Written Opinion for PCT/US2020/017588, dated Jun. 22, 2020, 18 pages.

*Primary Examiner* — Rebecca E Eisenberg
(74) *Attorney, Agent, or Firm* — Dority & Manning, P.A.

(57) ABSTRACT

A multi-headed catheter for fluid delivery and a method of placing a multi-headed catheter for fluid delivery are provided. The multi-headed catheter includes a first tube extending along an axis, wherein the first tube has at least one exit hole provided at a distal end of the first tube to define a perfusion section of the first tube; and a second tube extending along the axis, wherein at least a portion of the second tube is disposed within the first tube, wherein the second tube has at least one exit hole provided at a distal end of the second tube to define a perfusion section of the second tube. The distal end of the second tube is configured to exit said first tube at an opening provided along a wall of the first tube. The perfusion sections of the first tube and the second tube can be independently placed to deliver fluid to distinct anatomical areas within a surgical wound site.

21 Claims, 9 Drawing Sheets

(51) Int. Cl.
  *A61M 3/02* (2006.01)
  *A61M 19/00* (2006.01)
  *A61M 25/06* (2006.01)

(52) U.S. Cl.
  CPC .............. *A61M 2025/0681* (2013.01); *A61M 2205/3334* (2013.01)

(56) References Cited

U.S. PATENT DOCUMENTS

| | | |
|---|---|---|
| 5,978,103 A | 11/1999 | Martin |
| 6,156,016 A * | 12/2000 | Maginot ............ A61M 25/0028 |
| | | 604/533 |
| 6,350,353 B2 | 2/2002 | Deniega et al. |
| 7,465,291 B2 | 12/2008 | Massengale |
| 7,547,302 B2 | 6/2009 | Porto et al. |
| 7,569,045 B2 | 8/2009 | Deniega et al. |
| 8,992,454 B2 | 3/2015 | Anand |
| 9,656,043 B2 | 5/2017 | Bhagchandani et al. |
| 10,099,040 B2 * | 10/2018 | Agah .................. A61M 25/1011 |
| 2002/0198491 A1 * | 12/2002 | Miller .................. A61M 25/005 |
| | | 604/96.01 |
| 2003/0149395 A1 * | 8/2003 | Zawacki .............. A61M 1/3653 |
| | | 604/40 |
| 2004/0015138 A1 * | 1/2004 | Currier ............... A61M 25/007 |
| | | 604/525 |
| 2004/0030281 A1 * | 2/2004 | Goble .................... A61P 23/00 |
| | | 604/28 |
| 2005/0080398 A1 | 4/2005 | Markel et al. |
| 2009/0112153 A1 | 4/2009 | Gregersen et al. |
| 2009/0182265 A1 | 7/2009 | Mason |
| 2011/0224625 A1 * | 9/2011 | Flickinger ......... A61M 25/0105 |
| | | 604/257 |
| 2015/0306302 A1 * | 10/2015 | Marsden ............. A61M 25/003 |
| | | 604/95.04 |
| 2016/0303321 A1 * | 10/2016 | Kelly ................ A61M 25/0075 |
| 2017/0120011 A1 | 5/2017 | Burkholz et al. |

\* cited by examiner

MULTI-HEADED CATHETER FOR FLUID DELIVERY

FIELD OF THE INVENTION

The subject matter of the present invention relates generally to a catheter for fluid delivery, and more particularly to a multi-headed catheter having at least two lumens configured to independently deliver fluid to anatomical tissue within a surgical wound site.

BACKGROUND

Patient trauma, pain and discomfort resulting from surgery or other procedures is routinely managed through the administration of narcotics or non-narcotic drugs. Narcotics are generally disfavored as a pain management system because they affect the entire physical and mental well-being of the patient rather than only the local physical area of concern. Narcotics also have a variety of undesirable side effects, such as nausea, vomiting, bowel retention, respiratory depression, inhibition of the cognitive process, alteration of appetite, and potentially causing addiction. If used, narcotics can be administered through a variety of known ways, such as intra-muscular injection, epidural injection, intravenous injection, or orally.

Post-operative pain management is commonly addressed by administering non-narcotic drugs to the patient. Typically, the drug is administered directly into the epidural space of the patient for a period of several days following surgery, However, administering narcotics or non-narcotic drugs into the patient often necessitates monitoring by hospital staff and additional hospital stay due to the side effects of the drugs or because patients cannot be sent home with the required equipment to administer the drugs.

On-site drug administration procedure involves using a syringe and needle several times per day to inject the drug at or near the site where the surgeon made the incision through the patient's skin, with several needle pierces made during each dose application. Because many needle pierces are cumulatively made at or near the sensitive incision site, this administration procedure further aggravates patient trauma, pain and discomfort.

Another direct site drug administration procedure involves placing a drug directly into a wound site prior to a surgeon closing the wound. However, this procedure typically lasts only approximately four to six hours and patients often need pain management at a wound site for far in excess of this time period.

A further direct site drug administration procedure involves the placement of a catheter within the wound site prior to a surgeon closing the wound in order to deliver a low flow rate of anesthetic over a period of time (e.g., 2-5 days following surgery) to anesthetize the nerve bundles within the wound site. When coupled to a fluid pump, this procedure enables longer-term pain management than other existing procedures. However, this procedure enables delivery of the drug to just a single location within the wound, and pain management within a surgical site is often needed in multiple locations, for example, to block multiple nerves from causing pain or discomfort.

Consequently, a need therefore exists for a pain management system which reduces patient trauma, pain and discomfort resulting from surgery or other procedures. In particular, a pain management system which does not require repeated needle piercings at or near the sensitive incision site to deliver pain management drugs to multiple areas at or near the surgical wound would also be useful.

SUMMARY

The present invention provides a multi-headed catheter. The multi-headed catheter includes a first tube extending along an axis, wherein the first tube has at least one exit hole provided at a distal end of said first tube to define a perfusion section of said first tube; and a second tube extending along the axis, wherein at least a portion of the second tube is disposed within the first tube, wherein the second tube has at least one exit hole provided at a distal end of said second tube to define a perfusion section of said second tube. The distal end of said second tube is configured to exit said first tube at an opening provided along a wall of the first tube.

In one particular embodiment, a proximal end of the second tube is disposed within a proximal end of the first tube.

In another embodiment, the opening in the first tube can be located proximal to the perfusion section of the first tube.

In an additional embodiment, the at least one exit hole of the first tube and/or the at least one exit hole of the second tube can include a plurality of exit holes.

In yet another embodiment, the first tube and the second tube can be configured to connect with a multi-action pump to independently deliver fluid through the first tube and the second tube.

In still another embodiment, the perfusion section of the second tube can be configured to exit the first tube at the opening and extend outside of the first tube.

In an additional embodiment, the first tube can include a rigid port located at a proximal end of the first tube, wherein the rigid port of the first tube is configured to connect to a pump, further wherein the second tube can include a rigid port located at a proximal end of the second tube, wherein the rigid port of the second tube is configured to connect to the pump. Further, the rigid port of the first tube and the rigid port of the second tube can be configured to lock together to form a hub. Moreover, the proximal end of the rigid port of the first tube can include a locking tab, further wherein the distal end of the rigid port of the second tube can include a locking nut configured to receive the locking tab. In addition, the rigid port of the first tube can include a body extending along the axis and a connector extending at an angle to the axis, wherein the connector can be configured to connect to the pump.

In one another embodiment, the opening of the first tube comprises a self-sealing edge.

In one more embodiment, the second tube can be more rigid than the first tube.

The present invention additionally provides a fluid delivery system. The fluid delivery system includes a multi-headed catheter. The multi-headed catheter includes a first tube extending along an axis, wherein the first tube has at least one exit hole provided at a distal end of said first tube to define a perfusion section of said first tube; and a second tube extending along the axis, wherein at least a portion of the second tube is disposed within the first tube, wherein the second tube has at least one exit hole provided at a distal end of said second tube to define a perfusion section of said second tube; wherein the distal end of said second tube is configured to exit said first tube at an opening provided along a wall of the first tube. The fluid delivery system also includes a multi-action fluid pump configured to independently deliver fluid through the first tube and the second tube.

In one particular embodiment of the fluid delivery system, the first tube can be configured to be inserted into an anatomical region of a patient.

In another embodiment, the second tube can be configured to be inserted through a proximal end of the first tube.

In an additional embodiment, the distal end of the second tube can be configured to be located within the first tube during insertion of the first tube into an anatomical region of the patient.

In yet another embodiment, the distal end of the second tube can be configured to be pulled through the opening of the first tube after insertion and manually positioned at an anatomical location within the patient's body.

In still another embodiment, the fluid delivery system additionally can include an introducer comprising a tube configured to receive said first tube of the multi-headed catheter.

In a further embodiment, the multi-action fluid pump can be configured to deliver fluid through the first tube at a first flow rate and to the second tube at a second flow rate. Further, the first flow rate and the second flow rate can be not equal.

The present invention additionally provides a method of performing a nerve block. The method includes steps of: providing a multi-headed catheter comprising: a first tube extending along an axis, wherein the first tube has at least one exit hole provided at a distal end of said first tube to define a perfusion section of said first tube; and a second tube extending along the axis, wherein at least a portion of the second tube is disposed within the first tube, wherein the second tube has at least one exit hole provided at a distal end of said second tube to define a perfusion section of said second tube; wherein the distal end of said second tube is configured to exit said first tube at an opening provided along a wall of the first tube; providing a multi-action fluid infusion pump, the pump comprising a first tubing and a second tubing; inserting an introducer through the skin of a patient adjacent an open surgical wound site of the patient; advancing the introducer needle to the open surgical area; threading the first tube of the multi-headed catheter through the introducer to the open surgical wound site of the patient; pulling the second tube of the multi-headed catheter through the opening of the first tube of the multi-headed catheter; positioning the perfusion section of the second tube at a second location within the patient's body accessed by the open surgical wound site; positioning the perfusion section of the first tube at a first location within the patient's body accessed by the open surgical wound site; withdrawing the introducer from the patient then removing the introducer away from the first tube; connecting the first tubing of the pump to the first tube of the multi-headed catheter and connecting the second tubing of the pump to the second tube of the multi-headed catheter; and independently delivering fluid from the pump through the first tubing and the second tubing to the first location and the second location, respectively.

In one particular embodiment of the method, the first tube can include a rigid port located at a proximal end of the first tube, wherein the rigid port of the first tube can be configured to connect to a pump, further wherein the second tube can include a rigid port located at a proximal end of the second tube, wherein the rigid port of the second tube can be configured to connect to the pump; and the method further includes a step of locking the first rigid port to the second rigid port to form a unitary hub having a fluid-tight seal.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
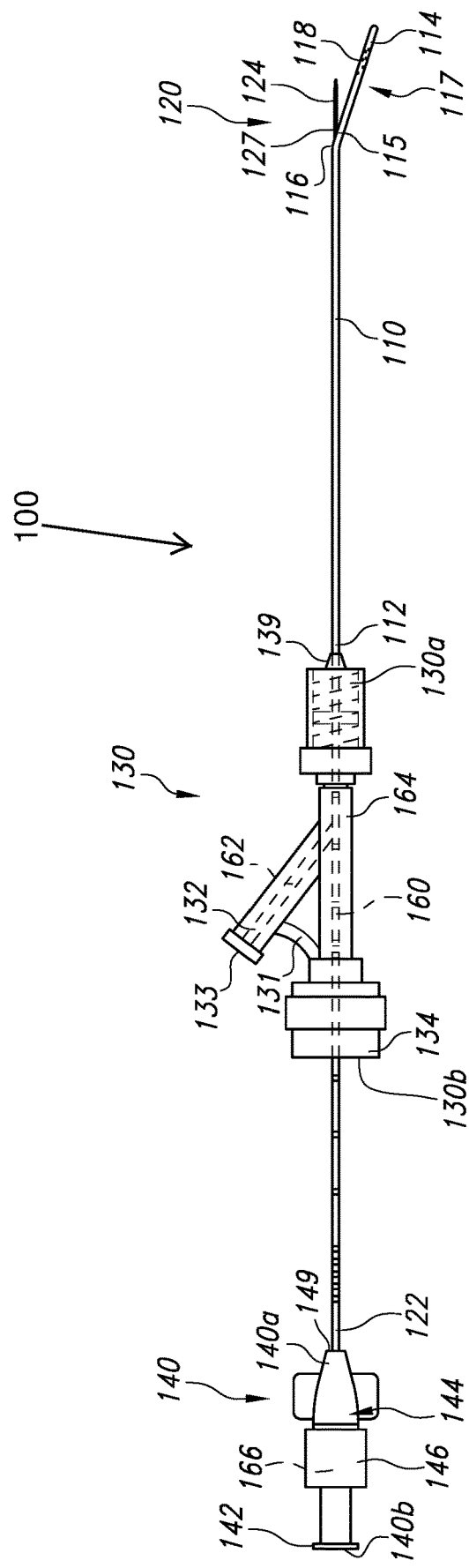
FIG. 1 illustrates a perspective view of a multi-headed catheter of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

To assist in the description of the system and method of use disclosed herein, the following terms are used. The "wound site" is the area within the body of the patient where the surgical procedure was performed. The "incision site" is the area where the surgeon entered through the patient's skin to arrive at the wound site. The incision site need not be made by the surgeon, for example, a patient may have an open wound through which the surgeon arrives at the wound site. The "pierce site" is the site where the patient's skin is pierced to allow the catheter to extend therethrough and arrive at the wound site to administer the drug.

The term "distal" refers to a site that is away from a specified site. The term "proximal" refers to a site that is close to a specified site. Expressed alternatively, a site termed "proximal" is measurably closer to a specified reference point than a site termed "distal." The term "downstream" refers to directional movement of the liquid drug from the infusion pump to the wound site. An object or site referred to as "downstream" of another object or site means that the "downstream" object or site is proximal the wound site relative to the other object or site. Similarly, an object or site referred to as "upstream" to another object or site means that the "upstream" object or site is proximal the infusion pump site relative to the other object or site. Expressed alternatively, the "downstream" object is proximal the wound site and the "upstream" object is distal the wound site.

Generally speaking, the present invention is directed to a multi-headed catheter that includes a first tube extending along an axis and a second tube extending along the axis. At least a portion of the second tube is disposed within the first tube. Each of the first tube and the second tube includes at least one exit hole provided at a distal end of the first tube and the second tube, respectively, to define a perfusion section of the first tube and a perfusion section of the second tube. The distal end of the second tube is configured to exit said first tube at an opening provided along a wall of the first tube. The first tube is connected to a first rigid port configured to deliver fluid to the first tube, and the second tube is connected to a second rigid port configured to deliver fluid to the second tube. The first rigid port and the second rigid port can be configured to connect to form a unitary hub. The specific features of the multi-headed catheter of the present invention may be better understood with reference to FIGS. 1-7.

FIG. 1 illustrates a multi-headed catheter 100 of one embodiment of the present invention. The multi-headed catheter 100 includes a first tube 110 and a second tube 120. Both the first tube 110 and the second tube 120 extend coaxially along the direction of an axis X. The second tube 120 has a smaller outer diameter than an inner diameter of the first tube 110 such that the second tube 120 can be disposed within the lumen 111 of the inner tube 110, as shown in FIGS. 1, 2A-C and 4.

As shown in FIG. 1, the first tube 110 extends from a proximal end 112 to a distal end 114 along the axis X. The first tube 110 includes a wall 117 surrounding a first lumen 111, illustrated in FIG. 4. Near to the distal end 114, the wall 117 of the first tube 110 includes at least one exit hole 118. In the embodiment shown in, e.g., FIG. 1, the first tube 110 includes a plurality of exit holes 118. The length of the segment containing the exit hole(s) 118 defines the perfusion section 119 of the first tube 110. The exit hole(s) 118 can be located radially along the wall 117 of the first tube 110 and/or the exit hole(s) 118 can be axially disposed at the distal end 114 of the first tube 110. The first tube 110 additionally includes an opening 116 in the wall 117 through which the second tube 120 can extend. The opening 116 has a self-sealing edge 115 that seals the opening 116 to prevent any leakage of fluid through the opening 116.

The first tube 110 of the multi-headed catheter 100 can be formed from a variety of materials, giving due consideration to the goals of flexibility, lightweight, strength, smoothness, and non-reactivity to anatomical systems, i.e., safety. Suitable materials for the first tube 110 include polyolefins, including polyethylene and polypropylene, polyamides, polyimides, teflon (polytetrafluoroethylene), polyesters, polyurethanes, any copolymers thereof, and other materials known in the art. A non-limiting example of a manufacture process suitable for forming the first tube 110 is the coextrusion of two tubes (coextrusion being a process known and understood by those having skill in the manufacture of extrude tubing), an outer tube and an inner tube, the inner tube being thinner and harder than the outer tube. Additional, non-limiting examples include utilizing reinforcement inserts such as a wire inside the wall 117 of the first tube 110, utilizing a spiral wound reinforcement, or utilizing a stabilizing mesh incorporated into the wall 117 of the first tube 110. Such reinforcements can extend along a length of the first tube 110 within the wall 117 extending between the proximal end 112 and the distal end 114, or any portion thereof, excluding the opening 116. Additionally or alternatively, the distal end 114 of the first tube 110 can be formed with a reinforcing material or materials including polyesters, polyurethanes, polyolefins, including polyethylene and polypropylene, polyester elastomer, tetrofluoroethylenes or polyamides such as a substituted or unsubstituted polyamide polymer, that may undergo additional reinforcement, such as by hardening or increasing the durometer of the polyamide, or by embedding a metal or metal alloy therein. By using a reinforcing material, the distal end 114 may be able to withstand the pressure applied to the first tube 110 during insertion.

The self-sealing edge 115 of the opening 116 of the first tube 110 can be formed from a soft polymeric material, e.g., silicone, polyurethane, polyvulcanate, polyvinylidene chloride (PVDC), polytetrafluoroethylene (PTFE), polysulphones, crosslinked elastomers, or other soft durometer materials. In one embodiment, an axial section 150 of the first tube 110 that includes the opening 116 can be formed from a soft polymer material that forms the self-sealing edge 115, and the remainder 152 of the first tube 110 can be formed from a firmer material to maintain the shape of the first tube 110 extending generally in the direction of the axis X.

The material and thickness of the wall 117 of the first tube 110 may be selected based upon the target location of the catheter, the likelihood of the need to reposition the first tube 110 of the catheter 100 after removal of the needle, and additional considerations. For example, a thicker body or a stronger material may be selected if the first tube 110 may need to be repositioned after removal of the needle or a thinner or weaker material may be selected so as to decrease bulk and potentially increase comfort in areas where the first tube 110 is less likely to need to be repositioned. It should also be noted that a reinforcing material may be used alone or in combination with a thicker or stronger material in situations where no needle, tunneler, or guidewire is needed, and instead the first tube 110 may be used without the tunneler, needle, or guidewire. A reinforcing material or a thicker or stronger body may also allow the first tube 110 of the present disclosure to be used independently, as compared to prior catheters which required the use of a sleeve or additional overlying materials in order to withstand the forces applied during placement.

In one possible configuration, the first tube 110 can be a 16 to 18 gauge catheter tube, having an outside diameter in a range from about 0.050 inches (1.27 mm) to 0.065 inches (1.65 mm). The first tube 110 can have a total length from proximal end 112 to distal end 114 in a range from about 12 inches (30 cm) to about 36 inches (91 cm), for example from about 18 inches (45 cm) to about 35 inches (90 cm), such as from about 24 inches (61 cm) to about 30 inches (76 cm).

The exit hole(s) 118 can have a diameter in a range from about 0.001 inches (0.025 mm) to about 0.03 inches (0.76 mm). In a further embodiment, some of the exit holes may have a fairly large diameter and some of the exit holes may have a fairly small diameter. In an embodiment with exit holes that have diameters of various sizes, the ratio of the diameter types may be fairly even, or in an alternate embodiment there may be more large diameter exit holes, such as two to five times as many large diameter exit holes. Alternatively, there may be more small diameter exit holes such as two to five times as many small diameter exit holes. The arrangement of the exit holes, number of exit holes, and diameter of the exit holes may be selected based upon the target area, the type of drug or anesthesia to be delivered, or the desired rate of delivery, to name a few considerations. For example, a larger number of exit holes or exit holes with a larger diameter, or both, may be selected when a greater rate of delivery is desired. Alternatively, arrangements of exit holes may be selected based upon the location and orientation of the target area. For example, if delivery of a drug to a small target area is desired, all of the exit holes may be located fairly close together either radially and/or axially. In an additional embodiment for example, if a target area is located on one side of the first tube 110, then the exit holes 118 may mainly be located on a single side of the first tube 110 such that the exit holes 118 are all located on generally the same side, area, or radius. Alternatively, if a more central location is chosen for placement of the first tube 110, the exit holes 118 may extend radially around the first tube 110 such that an aperture is located on several different radii around the first tube 110.

In embodiments having a plurality of exit holes 118, the exit holes 118 can be provided at equally spaced axial positions along the first tube 110. In a particular embodiment, the exit holes 118 can be arranged such that every hole 118 is angularly displaced by about 120 degrees relative to the longitudinal (X) axis of the first tube 110. The axial separation between adjacent exit holes 118 can be in a range from about 0.125 inches (3.175 mm) to about 0.25 inches (6.35 mm). The perfusion section 119 can have any desirable length. This configuration can result in a thorough, uniform delivery of fluid throughout a generally linear segment of the wound site. Of course, exit hole(s) 118 can be provided in any variety of alternative arrangements.

The perfusion section 119 of the first tube 110 can have any desired length, such as from about 0.5 inches (1.27 cm) to about 20 inches (51 cm) long, including all values and subranges therebetween. For example, the perfusion section 119 can be in a range from about 1 inch (2.5 cm) to about 15 inches (38 cm), such as from about 2 inches (3 cm) to about 12 inches (30.5 cm), e.g., from about 2.5 inches (6.3 cm) to about 5 inches (12.5 cm). In one particular embodiment the perfusion section 119 can be about 10 inches (25 cm) to about 12 inches (30.5 cm) long. Having a longer perfusion section 119 can reduce any impact to the fluid flow through the exit holes 118 in the perfusion section in the case of any occlusion of any of the exit holes 118. The perfusion section 119 is located between the opening 116 and the distal end 114 of the first tube 110. In an embodiment where the first tube 110 includes a single exit hole 118, the perfusion section 119 can be equal to the diameter of the exit hole 118.

In one embodiment, the exit holes 118 can have a smaller diameter nearer to the distal end 114 of the first tube 110 and a larger diameter further from the distal end of the tube. In another embodiment, the exit holes 118 are all equal in size so that the fluid is dispensed at a substantially equal rate through substantially all of the holes. The exit holes 118 can be formed by laser drilling, or other suitable methods, to achieve a very small hole diameter.

Figure 3:
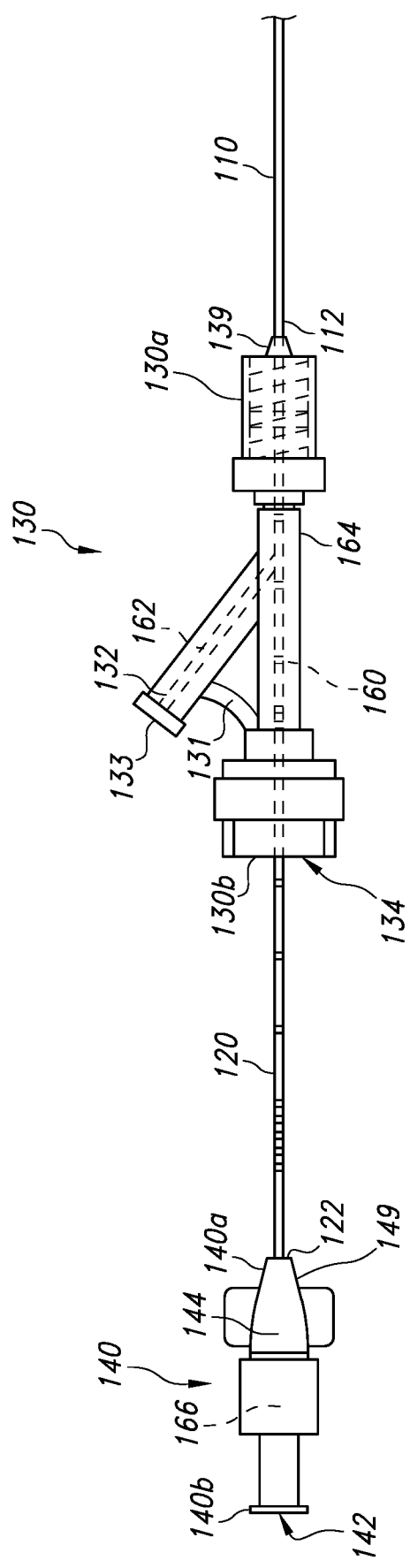
FIG. 3 illustrates a perspective view of the proximal end of the multi-headed catheter of FIG. 1.
Figure 4:
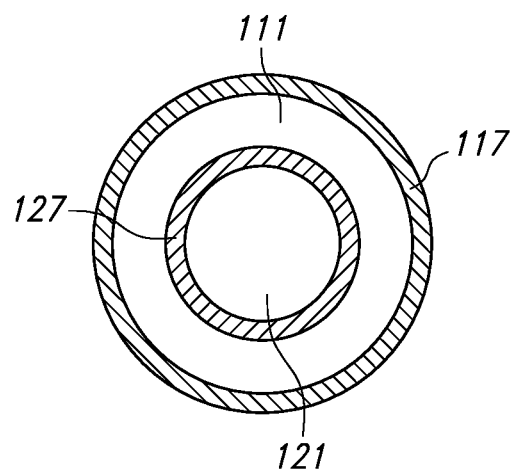
FIG. 4 illustrates a cross-sectional view of the multi-headed catheter taken along the line 4-4 of FIG. 2A.

As illustrated in FIGS. 1 and 3, the first tube 110 is connected at proximal end 112 to the first rigid port 130. The first rigid port includes a body 164 extending along the axial direction X from a distal body end 130a adjacent to the proximal end 112 of the first tube 110 to a proximal body end 130b. The first tube 110 connects to the distal body end 130a at a port connection 139 which forms a seal. A lumen 160 extends through the body 164 from the distal body end 130a to the proximal body end 130b along the axial direction X. The first rigid port 130 also includes a tubing connector 132 that can extend at an angle with respect to the body. The tubing connector 132 includes a fluid opening 133 for receiving fluid to be delivered by the first tube 110 and a fluid connector lumen 162 that extends from the fluid opening 133 to the lumen 160 of the body 164 of the rigid port 130. The tubing connector 132 is connected to the body 164 of the rigid port 130 by a support 131. As illustrated in FIG. 1, in one embodiment, the support 131 can be generally triangular shaped. The proximal body end 130a of the first rigid port 130 includes a port connector opening 134 in communication with the lumen 160 of the body 164.

Turning now to the second tube 120, as shown in FIG. 1, the second tube 120 extends from a proximal end 122 to a distal end 124 along the axis X. The second tube 120 includes a wall 127 surrounding a second lumen 121, also illustrated in FIG. 4. Near to the distal end 124, the wall 127 of the second tube 120 includes at least one exit hole 128. In the embodiment shown in, e.g., FIGS. 2A-C, the second tube 120 includes a plurality of exit holes 128. The length of the segment containing the exit hole(s) defines the perfusion section 129 of the second tube 120. The exit hole(s) 128 can be located radially along the wall 127 of the second tube 120 and/or the exit hole(s) 128 can be axially disposed at the distal end 124 of the second tube 120.

The second tube 120 of the multi-headed catheter 100 can be formed from a variety of materials, giving due consideration to the goals of flexibility, lightweight, strength, smoothness, and non-reactivity to anatomical systems, i.e., safety. Suitable materials for the second tube 120 include polyolefins, including polyethylene and polypropylene, polyamides, polyimides, teflon (polytetrafluoroethylene), polyesters, polyurethanes, any copolymers thereof, and other materials known in the art. A non-limiting example of a manufacture process suitable for forming the second tube 120 is the coextrusion of two tubes (coextrusion being a process known and understood by those having skill in the manufacture of extrude tubing), an outer tube and an inner tube, the inner tube being thinner and harder than the outer tube. Additional, non-limiting examples include utilizing reinforcement inserts such as a wire inside the wall 127 of the second tube 120, utilizing a spiral wound reinforcement, or utilizing a stabilizing mesh incorporated into the wall 127 of the second tube. Such reinforcements can extend along a length of the second tube 120 within the wall 127 extending between the proximal end 122 and the distal end 124, or any portion thereof. Additionally or alternatively, the distal end 124 of the second tube 120 can be formed with a reinforcing material or materials including polyesters, polyurethanes, polyolefins, including polyethylene and polypropylene, polyester elastomer, tetrofluorethylenes or polyamides such as a substituted or unsubstituted polyamide polymer, that may undergo additional reinforcement, such as by hardening or increasing the durometer of the polyamide, or by embedding a metal or metal alloy therein. By using a reinforcing material, the distal end 124 may be able to withstand the pressure applied to the second tube 120 during insertion. In some embodiments, the second tube 120 can be formed from a material that is more rigid than the material of the first tube 110 such that the second tube 120 can be easily advanced within the lumen 111 of the first tube 110.

In one possible configuration, the first tube 110 can be a 20 to 24 gauge catheter tube, having an outside diameter in a range from about 0.022 inches (0.56 mm) to 0.036 inches (0.91 mm). The second tube 120 can alternatively have any suitable inner and outer diameter to be able to be disposed within the first tube 110 and deliver fluid at an adequate flow rate to the patient's tissue. The second tube 120 can have a total length from proximal end 122 to distal end 124 in a range from about 12 inches (30.5 cm) to about 40 inches (102 cm), for example from about 18 inches (45 cm) to about 38 inches (97 cm), such as from about 24 inches (60 cm) to about 30 inches (76 cm).

The exit hole(s) 128 can have a diameter in a range from about 0.001 inches (0.025 mm) to about 0.03 inches (0.76 mm). In a further embodiment, some of the exit holes may have a fairly large diameter and some of the exit holes may have a fairly small diameter. In an embodiment with exit holes that have diameters of various sizes, the ratio of the diameter types may be fairly even, or in an alternate embodiment there may be more large diameter exit holes, such as two to five times as many large diameter exit holes. Alternatively, there may be more small diameter exit holes such as two to five times as many small diameter exit holes. The arrangement of the exit holes, number of exit holes, and diameter of the exit holes may be selected based upon the target area, the type of drug or anesthesia to be delivered, or the desired rate of delivery, to name a few considerations. For example, a larger number of exit holes or exit holes with a larger diameter, or both, may be selected when a greater rate of delivery is desired. Alternatively, arrangements of exit holes may be selected based upon the location and orientation of the target area. For example, if delivery of a drug to a small target area is desired, all of the exit holes may be located fairly close together either radially and/or axially. In an additional embodiment for example, if a target area is located on one side of the second tube 120, then the exit holes 128 may mainly be located on a single side of the second tube 120 such that the exit holes 128 are all located on generally the same side, area, or radius. Alternatively, if a more central location is chosen for placement of the second tube 120, the exit holes 128 may extend radially around the second tube 120 such that an aperture is located on several different radii around the second tube 120.

Figure 2A:
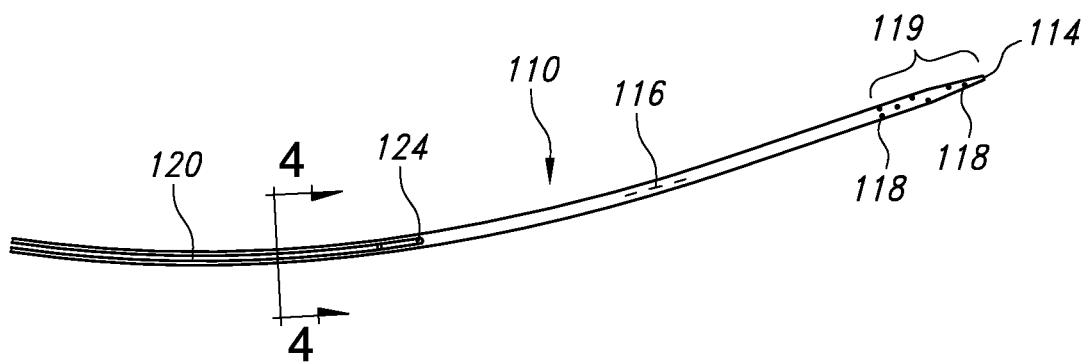
FIG. 2A illustrates a side view of the multi-headed catheter of FIG. 1 in a configuration having the distal end of the second tube positioned within the first tube.
Figure 2B:
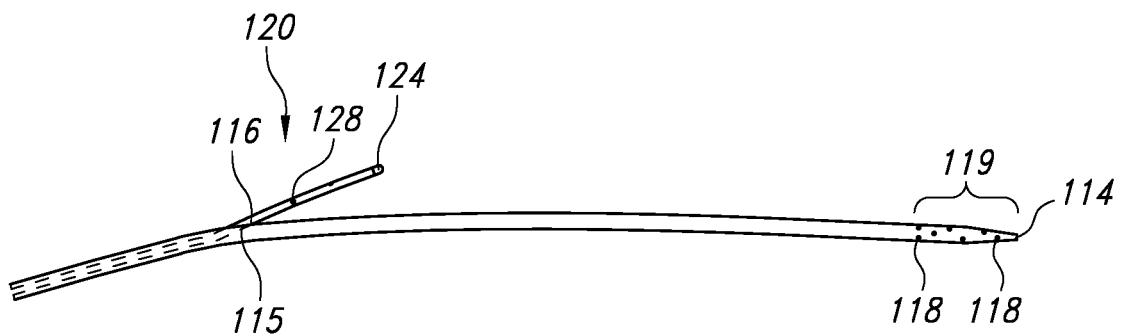
FIGS. 2B and 2C illustrate side views of the multi-headed catheter of FIG. 1 in a configuration having the distal end of the second tube extending through an opening within the first tube.
Figure 2C:
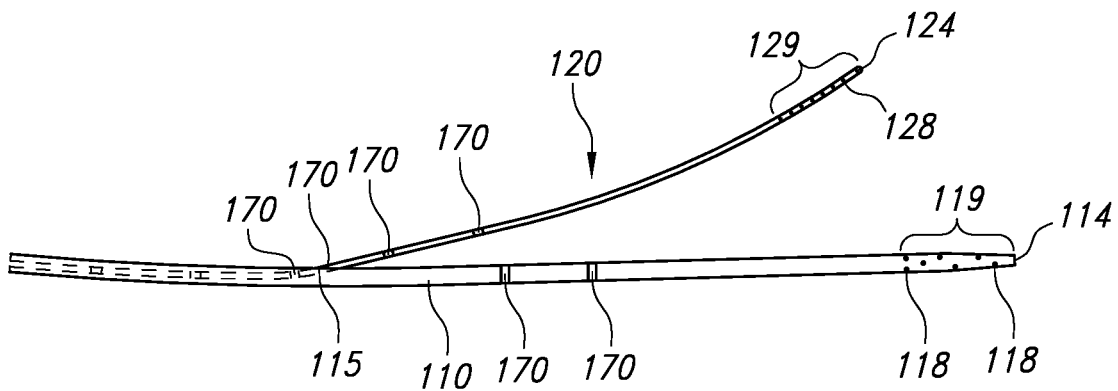

In embodiments having a plurality of exit holes 128, e.g., as shown in FIGS. 2A-C, the exit holes 128 can be provided at equally spaced axial positions along the second tube 120. In one particular embodiment, the exit holes 128 can be arranged such that every hole 128 is angularly displaced by about 120 degrees relative to the longitudinal (X) axis of the second tube 120. The axial separation between adjacent exit holes 128 can be within the range of about 0.125 to about 0.25 inches. The perfusion section 129 can have any desirable length. This configuration can result in a thorough, uniform delivery of fluid throughout a generally linear segment of the wound site. Of course, exit hole(s) 128 can be provided in any variety of alternative arrangements.

The perfusion section 129 of the second tube 120 can have any desired length, such as from about 0.5 inches (1.27 cm) to about 20 inches (51 cm) long, including all values and subranges therebetween. For example, the perfusion section 129 can be in a range from about 1 inch (2.5 cm) to about 15 inches (38 cm), such as from about 2 inches (3 cm) to about 12 inches (30.5 cm), e.g., from about 2.5 inches (6.3 cm) to about 5 inches (12.5 cm). In one particular embodiment the perfusion section 129 can be about 10 inches (25 cm) to about 12 inches (30.5 cm) long. Having a longer perfusion section 129 can reduce any impact to the fluid flow through the exit holes 128 in the perfusion section in the case of any occlusion of any of the exit holes 128. The perfusion section 129 is located adjacent to the distal end 124 of the second tube 120. In an embodiment where the second tube 120 includes a single exit hole 128, the perfusion section 129 can be equal to the diameter of the exit hole 128. In one embodiment, the exit holes 128 can have a smaller diameter nearer to the distal end 124 of the second tube 120 and a larger diameter further from the distal end 128 of the tube 120. In another embodiment, the exit holes 128 are all equal in size so that the fluid is dispensed at a substantially equal rate through substantially all of the holes. The exit holes 128 can be formed by laser drilling or any other suitable method to achieve a very small hole diameter. The holes are advantageously provided throughout the circumference of the perfusion section 129 of the second tube 120 to more uniformly deliver the fluid throughout an anatomical region.

In additional embodiments of the multi-headed catheter of the present invention, the multi-headed catheter can include more than two catheter tubes. For example, a multi-headed catheter can include a plurality of inner tubes each disposed within a first outer tube, such as two inner tubes, three inner tubes, four inner tubes, five inner tubes, or more than five inner tubes, wherein the outer tube can include self-sealing edge openings for each of the plurality of inner tubes. Further, it is to be understood that although not repeated in detail, any of the various features described above with respect to FIGS. 1-4 and multi-headed catheter 100 can be replicated and incorporated into a multi-headed catheter having more than two catheter tubes to the extent that such features do not conflict with the features required by a multi-headed catheter having more than two catheter tubes.

Figure 5A:
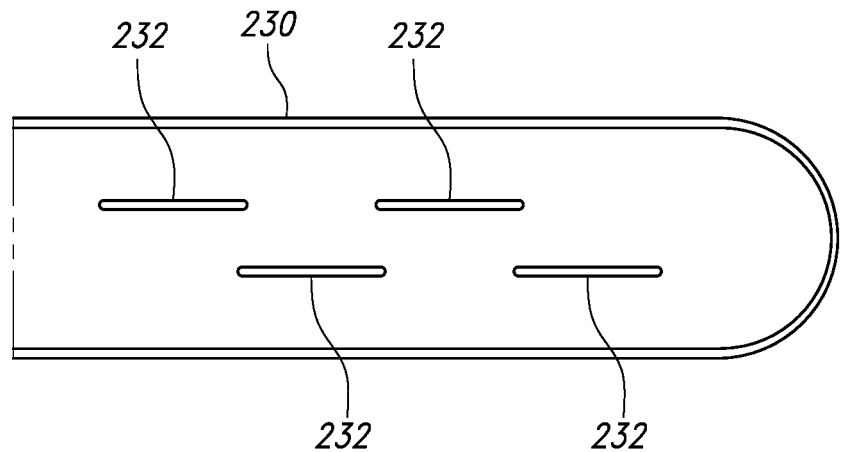
FIGS. 5A-B illustrate alternative embodiments of the exit holes of the multi-headed catheter of the present invention.
Figure 5B:
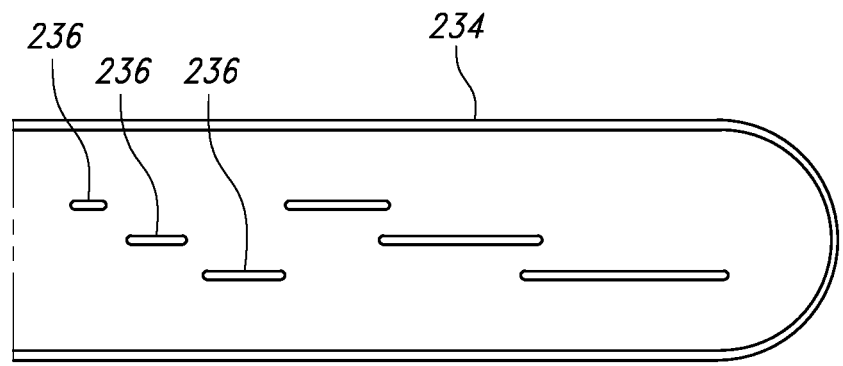

FIGS. 5A-B illustrate catheter tubes of an alternative embodiment of the present invention having elongated exit holes or slots. These catheter tubes may be used in place of the first and second catheter tubes shown and described above. FIG. 5A shows a tube 230 having exit holes or slots 232 that are elongated in the longitudinal direction of the tube 230. The slots 232 are preferably provided throughout the circumference of the tube 230, along the infusion section of the catheter. Compared to smaller exit holes, the elongated slots 232 tend to increase the flowrate of fluid exiting the catheter, by reducing the flow impedance experienced by the fluid. Preferably, the slots 232 may be oriented longitudinally on the catheter body so as not to compromise the structural integrity of the tube 230, as will be easily understood by those of skill in the art.

FIG. 5B shows a tube 234 having exit holes or slots 236 whose lengths increase along the length of the tube in the distal direction. In the illustrated embodiment, the slots nearer to the proximal end of the infusion section of the tube 234 are shorter in length than the slots nearer to the distal end of the infusion section. The catheter tube 234 advantageously provides substantially uniform fluid delivery through substantially all of the exit slots 236, under relatively high flow rate conditions. This is because the larger size of the more distal slots compensates for their increased flow resistance and pressure drop. In other words, since the more distal slots are larger than the more proximal slots, there is a greater flow rate through the more distal slots than there would be if they were the same size as the more proximal slots. Advantageously, the slots 236 are provided in a gradually increasing length, which results in substantially uniform fluid delivery. Further, the elongated slots can result in generally higher exit flowrates, as in the embodiment of FIG. 5B.

Of course, it is contemplated by the present inventors that one may provide larger or smaller exit holes or adjust the various distances between various exit holes and still achieve the results of the present invention. Thus, any such modifications are considered within the scope of the present invention.

Figure 6A:
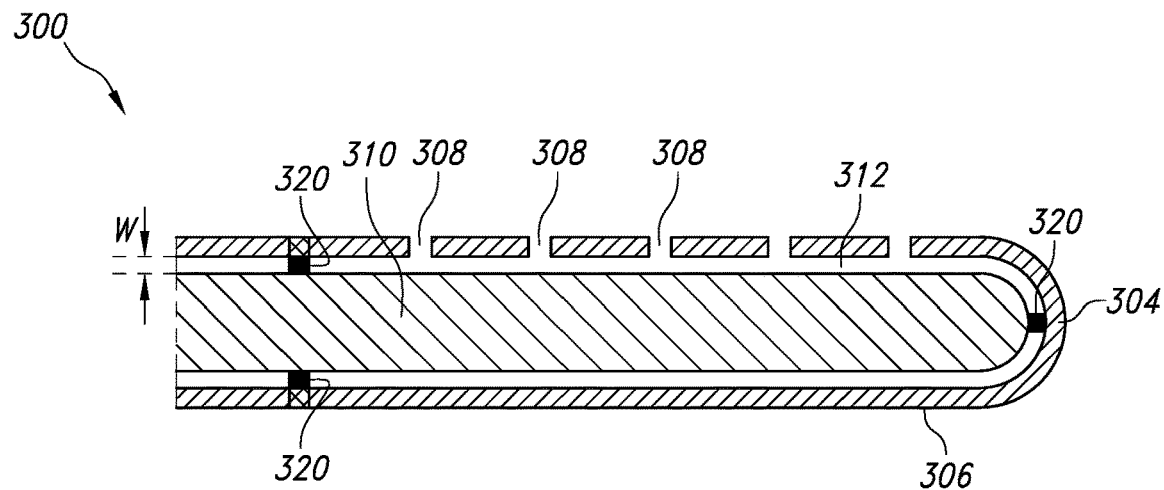
FIGS. 6A-B illustrates an alternative embodiment of a catheter tube of the multi-headed catheter of the present invention.
Figure 6B:
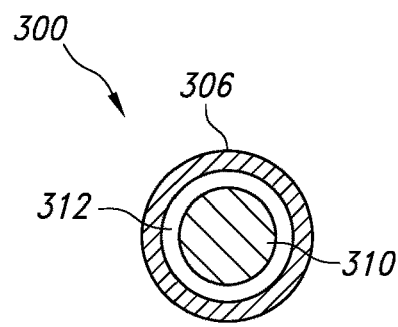

FIGS. 6A-B illustrate a catheter tube 300 of yet another embodiment of the present invention having an elongated member 310 formed of a porous material positioned within a distal end 304 of the catheter tube 300. These catheter tube 300 may be used in place of or in conjunction with any of the catheter tubes shown and described above. The distal end 304 of the catheter tube 300 can include a plurality of exit holes 308 therein along a perfusion section of the tube 306 of the catheter 304, and the elongated member 310 enclosed within the tube 306. Preferably, the elongated member 310 can be cylindrical in shape, solid, and made of a porous material. Preferably, the elongated member 310 is positioned within the tube 300 so that an annular space 312 is formed between the outer surface of the elongated member 310 and the inner surface of the tube 306. The elongated member 310 can extend from the distal end 304 of the tube 306 rearwardly to a point proximal of the perfusion section of the catheter 300. Alternatively, the elongated member 310 may extend along only a portion of the perfusion section. The elongated member 300 can preferably be disposed generally concentric within the tube 306, but non-concentric designs can achieve the advantages of the invention. In one embodiment, the elongated member 310 can be manufactured of a flexible material to assist with the placement of the catheter 300 in the body.

In operation, fluid flowing in the catheter tube 306 saturates the porous elongated member 310 and flows into the annular region 312. Once the porous elongated member 310 is saturated, the fluid in the porous elongated member 310 flows into the annular region 312 and out of the catheter 300 through the exit holes 308. Advantageously, since the fluid pressure is uniform throughout the annular region 312, the fluid flows substantially uniformly through all of the exit holes 308. There are several advantages of the annular region 312. One advantage is that it tends to optimize the uniformity of flow through the exit holes 308. Also, the elongated member 310 may be formed from a porous material that tends to expand when saturated with liquid. If so, the elongated member 310 preferably expands into the annular region 312 without pressing against the tube 306. This limits the possibility of high pressure regions at the interior surface of the tube 306, which could cause uneven exit flow of the medication within the wound site. Alternatively, the elongated member 310 may expand and come into contact with the tube 306, and still accomplish the goals of the present invention.

The elongated member 310 can be formed of a porous material having an average pore size within the range of 0.1 microns to 50 microns, for example about 0.45 microns. The radial width W of the annular region 312 can be within the range of 0 to about 0.005 microns, for example about 0.003 microns. The elongated member 310 can be formed of any of a variety of materials, giving due consideration to the goals of porosity, flexibility, strength, and durability. One example material is Mentek.

The elongated member 310 can be secured within the tube 306 by the use of an adhesive. In one embodiment, as shown in FIG. 6A, the adhesive is applied at the distal end of the elongated member to form a bond 310 with the interior surface of the distal end 304 of the tube 306. For example, adhesive can also be applied at or near the proximal end of the perfusion section of the catheter 300. Additionally, the adhesive can be applied to the circumference of the elongated member at any longitudinal position thereof, forming a ring-shaped bond with the interior surface of the tube 300. For example, in the embodiment of FIG. 6A, a ring-shaped bond 320 is provided just proximal of the perfusion section of the catheter. Other configurations are possible. Those of ordinary skill in the art will understand from the teachings herein that the adhesive may be applied in any of a variety of configurations. Thus, for example, adhesive at the distal end of the catheter is not required. The bonds 320 can be formed with an adhesive as described below.

A ring-shaped bond 320 can be formed by pouring the adhesive in liquid form through one of the exit holes 308 when the elongated member 310 is in the tube 306. The adhesive, having a generally high viscosity, tends to flow about the circumference of the elongated member 310, rather than into the body of the member 310. The adhesive thus forms a ring-shaped bond 320 with the tube 306, as will be understood by those of skill in the art. Also, the adhesive plugs the exit hole 308 through which it is poured. Any of a variety of different types of adhesives will be acceptable, a preferred adhesive being Loctite.

As mentioned above, the elongated member 310 can be concentric with the tube. FIG. 6B shows a cross-section of a catheter 300 in which the elongated member 310 is concentrically enclosed within the tube 306. Alternatively, the elongated member 310 may be positioned adjacent to the tube 304 (not shown), which can be easier to manufacture than the configuration of FIG. 6B since the elongated member 310 does not have to be centered within the tube 306.

Those of ordinary skill in the art will understand from the teachings herein that the elongated member 310 can be of any desired length and can extend along any desired length of the perfusion section of the catheter 300. For example, the elongated member 300 does not have to extend to the distal end 304 of the tube 306. Further, the proximal end of the elongated member 310 may be either distal or proximal to the proximal end of the perfusion section.

Figure 7:
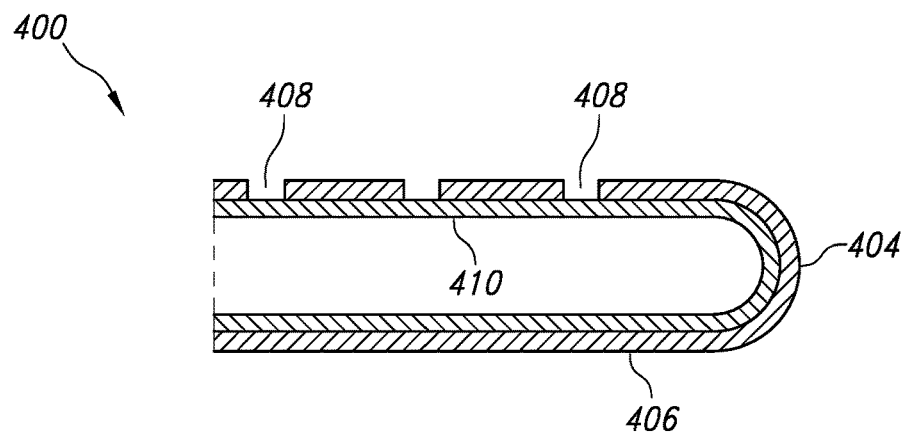
FIG. 7 illustrates yet another alternative embodiment of a catheter tube of the multi-headed catheter of the present invention.

FIG. 7 illustrates a catheter tube 400 of yet another embodiment of the present invention having an inner tubular membrane 410 formed of a porous material positioned within a distal end 404 of the catheter tube 406. The catheter tube 400 may be used in place of or in conjunction with any of the catheter tubes shown and described above. The distal end 404 of the tube 406 of the catheter 400 can include a plurality of exit holes 408 therein along a perfusion section of the catheter 400, and the inner tubular membrane 410 can be concentrically enclosed within the tube 406. For example, the catheter tube 406 can tightly surround and support the inner tubular membrane 410 so that a relatively tight fit is achieved between the inner dimensions of the catheter tube 406 and the outer dimensions of the tubular membrane 410. The tubular membrane 410 need only be provided along the length of the perfusion section, but could be longer.

The tubular porous membrane 410 can be a sponge-like or foam-like material or a hollow fiber. The tubular membrane 410 may have an average pore size, or pore diameter, less than 0.23 microns to filter bacteria. The pore diameter can be within the range of about 0.1 to 1.2 microns, such as within the range of about 0.3 to 1 micron, for example about 0.8 microns. The tubular membrane 410 may be formed from any of a variety of suitable materials, giving due consideration to the goals of non-reactivity to anatomical systems, maintaining flexibility, fitting within the size constraints of the catheter tube, and having a porosity resulting in the substantially uniform dispensation of fluid through all of the exit holes in catheter tube. Some suitable materials for the membrane are polyethylene, polysulfone, polyethersulfone, polypropylene, polyvinylidene difluoride, polycarbonate, nylon, or high density polyethylene. Example inside and outside diameters of the tubular membrane 410 are 0.010 inches and 0.018 inches, respectively, but one of ordinary skill in the art should understand that the inside and outside diameters of the tubular membrane 410 are dependent on the inner diameter of the catheter tube. The catheter tube 406 may be secured to the membrane 410 by epoxy or other means known to those skilled in the art. Alternatively, the membrane 410 may contact the catheter tube 406 with an interference fit and not use other materials to secure the membrane 410 in the catheter tube 406.

In operation, the catheter 400 can deliver fluid to the region of an anatomical system adjacent to the perfusion section of catheter 400. As the fluid flows into the perfusion section, it initially soaks into the tubular porous membrane 410. As more fluid enters the perfusion section, the fluid diffuses longitudinally within the walls of the tubular member 410. Once the membrane 410 and the tubular space therein are saturated, the fluid passes through the membrane 410 and exits the catheter 400 by flowing through the exit holes 408 of the catheter tube 406. Moreover, the fluid advantageously passes through the membrane 410 substantially uniformly throughout the surface area of the membrane 410, resulting in a substantially uniform flow through substantially all of the exit holes 408. Thus, the fluid is delivered at a substantially equal rate throughout the wound area of the anatomy. Furthermore, this advantage is obtained for both low and high pressure fluid delivery.

In another embodiment of a catheter tube of the present embodiment (not shown), the catheter tube can include a compressible reservoir upstream of perfusion section near to the proximal end of the catheter. The compressible reservoir can be, e.g., a compressible balloon in communication with the catheter tube, or a portion of the catheter tube having a widened diameter, or any other suitable compressible reservoir structure. This feature can be beneficial in overcoming an occluded catheter tip, e.g. occlusion of the exit holes in the perfusion section of the catheter. When an occlusion occurs, a doctor or other health care professional to compress the compressible reservoir to blow-out the occluded tip by squeezing additional fluid at a high pressure through the catheter.

Turning back to FIGS. 1 and 3, the second tube 120 is connected at proximal end 122 to the second rigid port 140. The second rigid port 140 extends along the axial direction X from a distal end 140a adjacent to the proximal end 122 of the second tube 120 to a proximal end 140b. The second tube 120 connects to the distal end 140a at a port connection 149 which forms a seal. A lumen 166 extends through the second rigid port 140 from the proximal end 140b to the port connection 149 connecting to the second tube 120 along the axial direction X. The proximal end 140a of the second rigid port 140 includes a fluid connector opening 142 in communication with the lumen 166 of the second rigid port 140.

As illustrated in FIGS. 1 and 2A-C, the second tube 120 is configured to be inserted through the port connector opening 134 of the first rigid port 130, through the lumen 160 of the body 164 of the first rigid port 130, through the first tube 110 and exit through the opening 116 of the first tube 110. As shown in FIG. 2A, the distal end 124 of the second tube 120 can be disposed within the first tube 110. FIG. 2B shows the distal end 124 of the second tube 120 extending from the opening 116 of the first tube 110, and FIG. 2C shows the entire perfusion section 129 of the second tube 120 along with additional length of the second tube 120 protruding from the opening 116 of the first tube 110 such that the first tube 110 and the second tube 120 extend approximately a same distance in the x-direction. FIG. 2C additionally shows markings 170 along the second tube 120. The markings 170 can indicate the distance that the second tube 120 extends relative to the opening 116, for example. The markings 170 can additionally be used to ensure that the entire tube 120 is removed from a patient's body, e.g., by checking for the presence of a certain number or pattern of markings 170. In other embodiments, the first tube 110 can also include markings 170 to gauge distance or to check for removal of the entire first tube 110. The markings 170 on the first tube 110 and the second tube 120 can have the same pattern or different patterns.

In use, the multi-headed catheter 100 is inserted into an anatomical system, such as a human body, to deliver fluid medication directly to a wound site within the anatomical system. In particular, the multi-headed catheter 100 is designed to deliver medication throughout two discrete areas of the wound site corresponding to the perfusion sections 119 and 129 of the first tube 110 and the second tube 120, respectively, of the multi-headed catheter 100. Thus, the multi-headed catheter 100 is preferably inserted so that the perfusion sections 119 and 129 are positioned within the wound site or at anatomical areas known to block nerves that cause pain at the wound site.

In operation, the multi-headed catheter 100 delivers fluid directly to the area of the anatomy that is adjacent to the perfusion sections 119 and 129. The fluid from the fluid source is introduced into the lumen 111 of the first tube 110 through the fluid connector port 132, and into the lumen 121 of the second tube 120 through the fluid connector port 142. The fluid initially flows through the proximal end 112 of first tube 110 and through proximal end 122 of second tube 120 through the non-perfusing section. When the fluid reaches the infusion sections 119 and 129, it diffuses through the exit holes 118 and 128, respectively.

Figure 8:
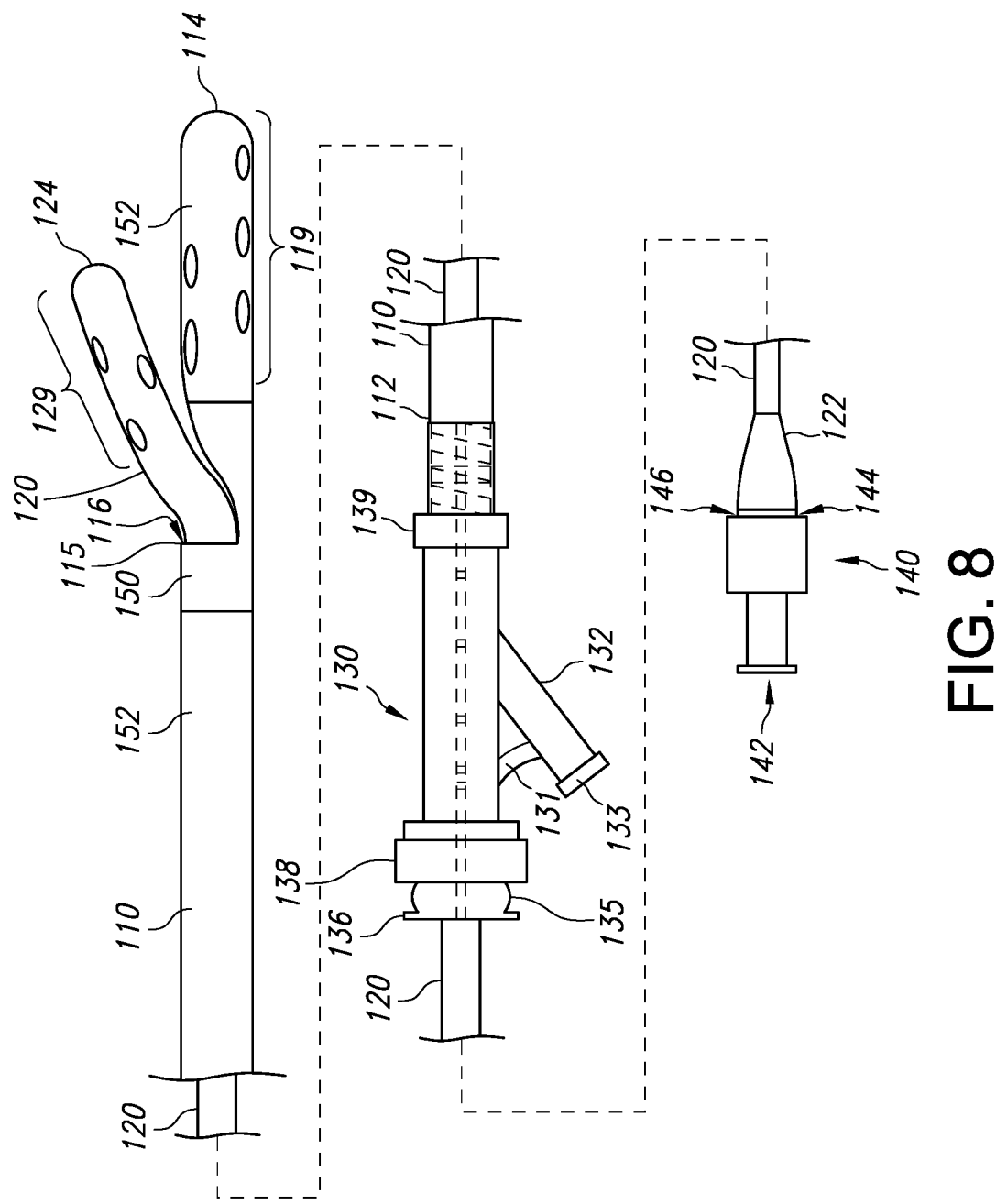
FIG. 8 illustrates an exploded view of the multi-headed catheter of FIG. 1.
Figure 9:
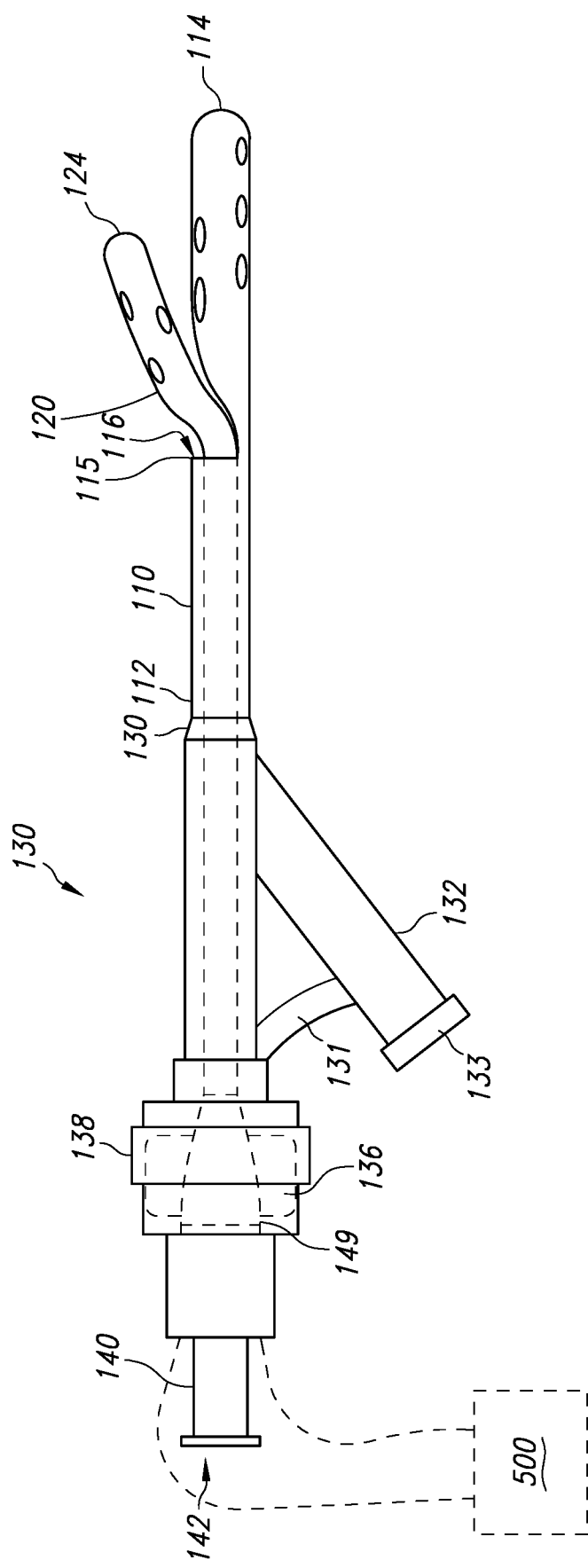
FIG. 9 illustrates the multi-headed catheter of FIG. 1 having the first rigid port and second rigid port connected to form a unitary hub.

After positioning the first tube 110 and second tube 120 within the wound site, the first rigid port 130 and the second rigid port 140 can be connected and sealed together to form a unitary hub 170, as shown in FIG. 7. A locking tab 136 at the distal body end 130b of the first rigid port 130 fits within port connector opening 144 of the second rigid port 140 and can mate with a corresponding locking tab 136, which can then be secured by a locking nut 138 of the first rigid port 130. The locking tab 136 can include a sealing material 135 around its periphery (see FIG. 8) in order to form a fluid-tight seal at the junction of the first rigid port 130 and second rigid port 140 to prevent leakage of fluid from the lumen 160 of the body 164 of the first rigid port 130.

When the multi-headed catheter 100 is used, the catheter 100, i.e. the tubes 110 and 120, may initially contain air. The introduction of liquid medication into the catheter forces the air to flow out of the exit holes. However, this may take several hours. If either of the tubes 110 or 120 is inserted into a patient while air is inside, and liquid medication is introduced into the tube, the patient's wound site may receive little or no medication until air is expelled from the tube. Thus, it is preferred to run liquid through the catheter or tube prior to inserting the tubes 110, 120 of the multi-headed catheter 100 into the patient, to ensure that the air is expelled prior to use.

In some embodiments, the first tube 110 and/or the second tube 120 of the multi-headed catheter 100 can also include anti-microbial properties to inhibit the growth of microbes on or within the catheter and, preferably, to inhibit microbe growth in an anatomical region adjacent the catheter. As described in greater detail below, the illustrated catheters may include an anti-microbial layer, anti-microbial materials embedded within the material from which components of the catheters are constructed, or a combination of anti-microbial layers and embedded anti-microbial materials.

In preferred arrangements, the anti-microbial layers or materials are configured to provide the sustained release of anti-microbial agents. In one arrangement, the anti-microbial layer or material comprises a heavy metal such as gold, platinum, silver, zinc or copper, all of which are known to possess anti-microbial properties and, more preferably, the heavy metal is in the form of metal ions. In a particularly preferred embodiment, the anti-microbial layer or material is silver and, more preferably, silver ions. However, other anti-microbial substances such as antibiotics or germicidal chemicals may also be used or incorporated on or in the catheter.

In some arrangements, the metal ions may be contained within a carrier material, such as a natural or synthetic polymer, which preferably assists in the sustained release of the metal ions and inhibits degradation of the metal ions. Other suitable methods for providing for the sustained release of the anti-microbial substances may also be used.

As described above, in certain arrangements, the anti-microbial material may be in the form of a layer of material making up a portion of a component of the catheter, such as the tubular catheter body or a flow control component, for example. To create such an anti-microbial layer, the anti-microbial material may be applied as a coating to a component of the catheter, such as by a deposition, dipping, spraying, co-extrusion, or other techniques or processes suitable for creating a multi-layered article.

In alternative arrangements, the anti-microbial material may be dispersed within the base material(s) that construct a component of the catheter, such that the base material forms an anti-microbial layer. For example, the anti-microbial material may be compounded or otherwise embedded or dispersed within the polymer material forming the catheter body. However, the anti-microbial material may be embedded within other components of the catheter, as described in greater detail below. The anti-microbial material may be provided within the base material prior to the process of manufacturing the catheter component. For example, the anti-microbial material may be provided within the polymer resin used to create the catheter body by extrusion or other forming processes.

Preferably, the anti-microbial substance is both embedded within a base material of the catheter tube or other catheter components and forms a layer on the tube or other component(s). In one particularly preferred arrangement, the anti-microbial substance comprises stabilized ionic silver nanoparticles, which preferably are less than about 50 nm in size and, more preferably, are between about 5 to 15 nm in size, in a solution.

The catheter (or catheter component) is preferably submerged into the solution, which in one arrangement may comprise silver chloride with a reducing agent. The catheter preferably is submerged in the solution for a period of time sufficient to permit the silver particles to adhere to the catheter. In one arrangement, the catheter is submerged for about 16 hours in a solution that is above room temperature. For example, the temperature of the solution may be approximately 35 degrees Celsius. Desirably, multiple catheters are submerged in a container of solution at the same time. Preferably, the solution and/or catheters are agitated to assist in providing a uniform silver particle distribution throughout the length of the catheters and, desirably, on both inner and outer surfaces of the catheters. In one preferred method, the catheter body (or tubular portion of the catheter assembly) is treated with the anti-microbial substance separate from the flow control components, such as those described above. If desired, the flow control components, such as the hollow fiber member or membrane, may be treated with the anti-microbial substance separately. The catheter body and flow control component(s) may then be assembled.

Once the catheters have been submerged in the silver solution for a desirable period of time, the catheters are removed from the solution and, preferably, rinsed. The rinsing agent is alcohol in one preferred method of manufacture. After rinsing, the catheters are allowed to dry. If desired, means may be provided to assist the drying of the catheters. For example, the catheters may be spun. In one arrangement, the catheters are spun at approximately 80-100 rpm for about two minutes. After spinning, the catheters preferably are allowed to fully dry, preferably overnight.

The dried catheters preferably are then exposed to light. Catheters which have been submerged in silver solutions and are then exposed to light change in color or become colored. For example, typical nylon catheters usually are clear or opaque and become colored after submersion in the silver particle solution. Catheters exposed to certain silver solutions, such as those disclosed herein, may take on a gold or amber coloration. The coloration of such catheters enhances the ease of identification of treated catheters in contrast to untreated catheters. It is believed that the silver treated catheters described herein are the only non-clear, or colored, catheters used for wound site, peripheral nerve block or epidural applications and, thus, the coloration will provide the advantage of easy identification that the catheters possess anti-microbial properties.

During the submersion of the catheters, the nanoparticles are able to become lodged in surface imperfections in the catheter tube, or other components, such as the flow control membrane (hollow fiber), for example. Furthermore, due to their small size and charge, the silver nanoparticles tend to stick to the surface of the catheter tube or other component that is being treated. Thus, in this preferred arrangement, the anti-microbial substance is both impregnated and coated onto the catheter. The catheters are then dried. The silver ions are then released over time when the catheter comes into contact with moisture, such as when placed within a body.

The silver nanoparticles may be created by any suitable process. In one preferred arrangement, the silver nanoparticles are prepared by adding a reducing agent to silver chloride. Such compositions are well-suited for use in the commercial scale manufacture of medical devices, such as the catheters disclosed herein. However, other suitable methods of producing silver nanoparticles may also be used. In a preferred arrangement, the catheter body is constructed from a nylon material and the anti-microbial material is applied to and/or impregnated within the nylon.

Preferably, the anti-microbial substance is configured for sustained release by the catheter. In a fluid delivery catheter, the anti-microbial substance may be released into the fluid, and carried by the fluid into the anatomical region adjacent the catheter. Such an arrangement advantageously inhibits microbe growth both in the catheter and in the region adjacent the catheter, as the anti-microbial substances are likely to travel a greater distance within the anatomical region with the fluid being dispensed than when only released to the tissue from the catheter body itself. Accordingly, it is preferred that the catheter is configured to release anti-microbial substances into the fluid being dispensed, such as by treating the internal (lumen-defining) surface of the catheter or the above-described flow control components. In the case of a wound site pain management application, advantageously, such a catheter would not only provide pain management substances, but would also inhibit microbe growth, and infection, in the wound site.

Preferably, the catheter is configured to release an anti-microbial substance at an elution rate of between about 0.8 and 3.0 µg/cm for at least the infusion section of the catheter and, preferably, for at least the entire portion of the catheter internal to the patient. Preferably, the catheter is configured to maintain such an anti-microbial release over an expected duration of use of the catheter. In one arrangement, the catheter is configured to maintain a significant release of an anti-microbial substance for a minimum of 10 days.

In addition, in some preferred arrangements, the catheter is configured to release a greater amount of an anti-microbial substance initially (a bolus dose) and then maintain a lesser dose thereafter. For example, in one preferred arrangement, the catheter releases a greater amount of an anti-microbial substance for the first 5 days after placement and then maintains a substantially constant lower level of release for at least about 5 days thereafter. However, in other arrangements, release of the anti-microbial substance may be relatively constant or may decline over time in a generally linear fashion. For a 20 gauge catheter, preferably, about 15% of the silver particle content is released within about 10 days. In other applications, however, a lesser or greater release of anti-microbial substances or agents may be desired.

Preferably, the catheter is treated to contain, or is loaded with, a sufficient amount of the anti-microbial substance to obtain desirable elution rates. The anti-microbial content of the catheter may be varied by altering the time of submersion in the anti-microbial substance solution, for example. In a 20 gauge catheter containing silver nanoparticles, it is preferred that the catheter be loaded to a level such that the ratio of silver particles to the base material of the catheter (or treated catheter component) is about 600-2000 parts per million (ppm). In one preferred arrangement, the catheter is loaded to a level of about 1000 ppm. Such silver nanoparticle contents were determined to produce satisfactory elution rates which encompassed the above-recited ranges. For example, a catheter containing approximately 600 ppm, the elution rate was found to average approximately 1.8 µg/cm for the first 5 days and approximately 0.8 µg/cm for the next 5 days. A catheter containing approximately 1000 ppm provided an elution rate of about 3.0 µg/cm for the first 5 days and about 1.4 pg/cm for the next 5 days. In addition, the silver nanoparticle contents of the catheter may be modified to produce other desired elution rates.

As will be easily understood by those of skill in the art, any of the catheter embodiments described herein may be used in a variety of applications including, but not limited to, peripheral nerve blocks, intrathecal infusions, epidural infusions, intravascular infusions, intraarterial infusions and intraarticular infusions, as well as in wound site pain management. Furthermore, the disclosed multi-headed catheters may be adapted for use as aspiration catheters, as well.

In addition, any of the multi-headed catheters disclosed herein may be integral with a fluid line emanating from an infusion pump as opposed to being an independent catheter designed to be connected or secured to an infusion pump. The multi-headed catheter 100 disclosed herein can be connected or secured to a multi-action fluid pump 500 having at least two fluid connectors and at least two flow selectors, respectively, such that fluid can be delivered through the first tube 110 and the second tube 120 at independent, e.g. unequal, flow rates.

In one exemplary surgical method, the multi-headed catheter 100 of the present invention can be used to multi nerve block for treatment of post-surgical total knee arthroplasty (TKA) pain. The catheter 100 can be inserted intraoperatively into the medial intermuscular septum to provide a continuous adductor canal and periarticular nerve block. A preferred procedure to insert the multi-headed catheter into the patient's body through a piercing site will be described below.

The multi-headed catheter 100 can be inserted during a medial parapatellar, midvastus, or subvastus approach to the TKA. The medial parapatellar procedure is performed by incising the vastus medialis oblique muscle beginning medially just above the patella and extending down to the tibial tubercle, leaving a cuff of capsular tissue on the patella for repair at closure. For the mid-vastus approach, the vastus medialis oblique muscle is split in-line with the muscle fibers at the superior pole of the patella and then incised distally to the tibial tubercle. The subvastus approach to TKA begins with an incision below the vastus medialis oblique muscle and extends to the tibial tubercle.

After the surgical approach to the knee, described above, the adductor tubercle of the epicondyle of the femur is identified. Then, the vastus medialis oblique muscle is elevated with blunt retractors to expose its deep surface and the anterior surface of the medial intermuscular septum. The medial intermuscular septum will serve as the floor for the placement of the multi-headed catheter 100. The adductor magnus tendon can be palpated beneath the medial intermuscular septum just cephalad (in the direction of the patient's head) to the adductor tubercle. The vastus medialis oblique muscle and the adductor magnus muscle form the borders of the adductor canal. As defined above, the open surgical site is considered to be the wound site for placement of the multi-headed catheter 100.

Figure 10:
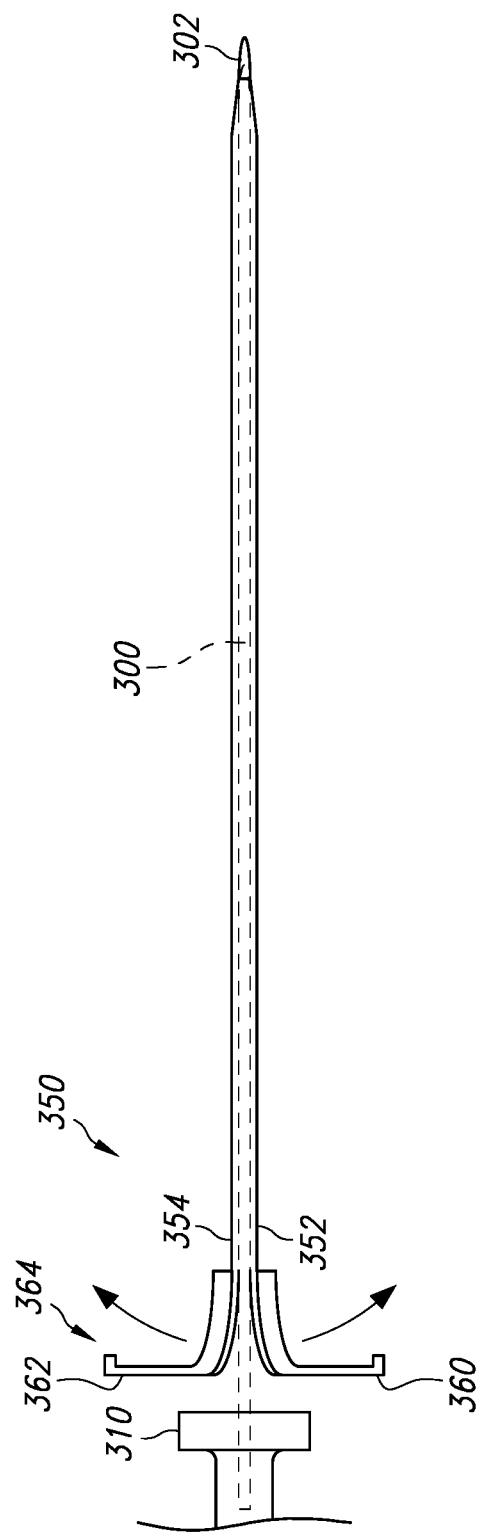
FIG. 10 illustrates an exemplary introducer-needle assembly for insertion of the multi-headed catheter of the present invention.

As illustrated in FIG. 10, an introducer needle 300 is provided for insertion of the multi-headed catheter 100. The introducer needle 300 comprises a conventional medical needle or rod having a pointed end 302 sufficiently sharp to pierce and penetrate the patient's skin. The introducer needle 300 may be hollow or solid without any lumen therethrough. The introducer needle 300 can include a stopper 310 at an end opposite the pointed end 302. An introducer tubing or sheath 350, such as a T-peel sheath, has a diameter sufficient to allow the introducer needle 300 to be place therein. The introducer tubing 350 or sheath is sufficiently rigid so that it can extend through the piercing site and into the patient's body without significantly bending away from the introducer needle 300 upon penetration through the skin, yet includes a defined pattern of reduced strength to direct the separation of the sheath 350 into split portions 352 and 354 to be pulled apart and removed from the catheter. For example, a T-peel sheath includes a T-shaped handle 364 having opposing hand-grip portions 360 and 362 and one or more score lines or portions having a thickness less than the thickness of another portion of the sheath 350. The stopper 310 of the introducer needle 300 can have a width sufficient to prevent the stopper 310 from moving beyond the T-shaped handle 364 when the introducer needle 300 is inserted into the sheath 350.

At least a portion of the introducer needle 300 is placed within at least a portion of the introducer sheath 350 to form a needle/sheath assembly 370. When the needle/sheath assembly 370 is formed, the end 302 of the introducer needle 300 preferably extends beyond the end of the introducer sheath 350 so that the end 302 of the introducer needle 300 initially pierces the patient's skin at the piercing site and then the end of the introducer sheath 350 extends through the piercing site.

The needle/sheath assembly 370 cooperates so that when the introducer needle 300 and the introducer sheath 350 pierce the skin and are advanced into the patient to form a passage, neither the introducer needle 300 nor the introducer sheath 350 appreciably move relative to each other, yet, when the introducer needle 300 is withdrawn, the introducer needle 300 separates from the introducer sheath 350 and at least a portion of the introducer sheath 350 remains within the patient.

Figure 11:
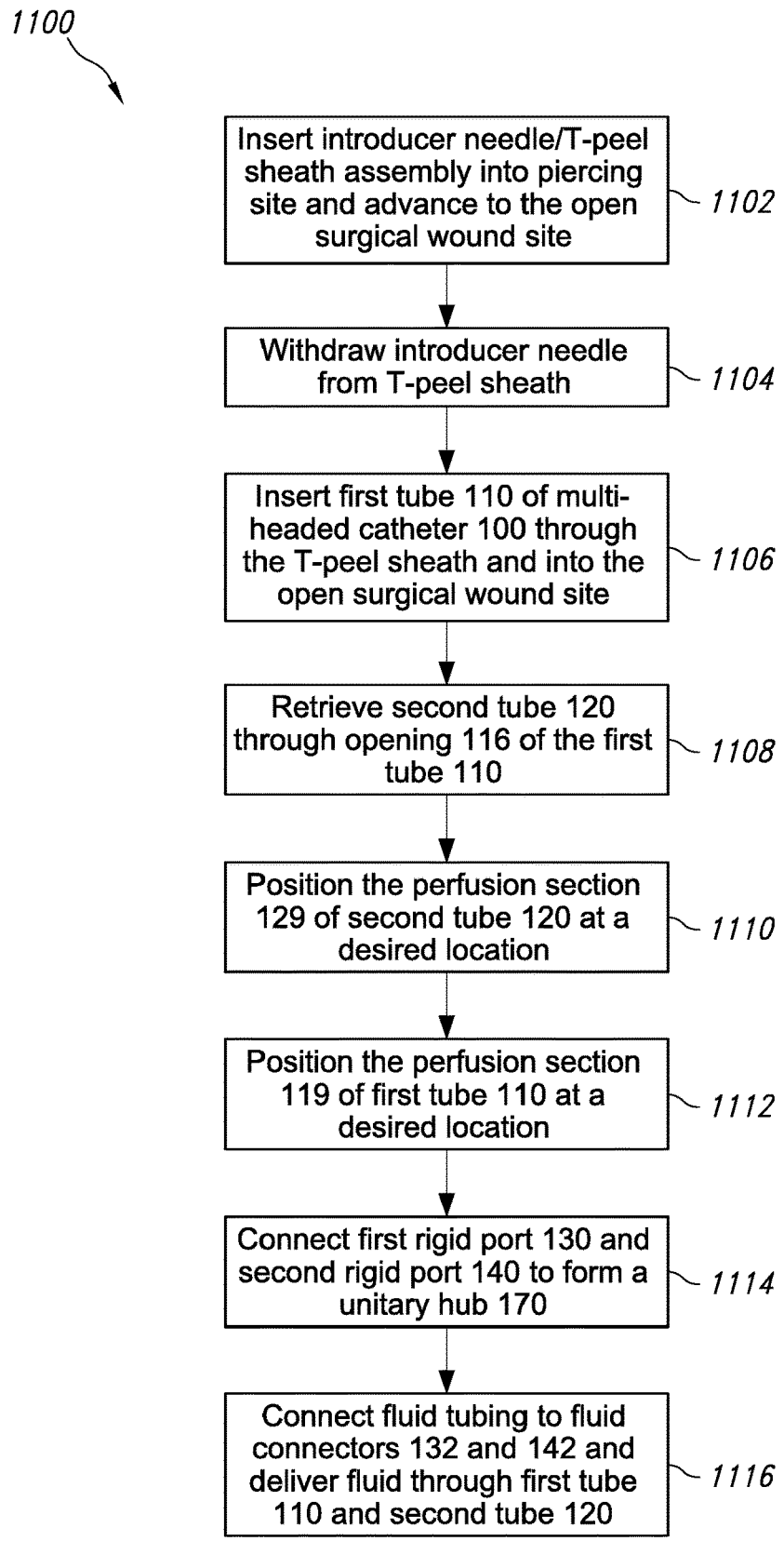
FIG. 11 illustrates a method of placing the multi-headed catheter of FIG. 1 for fluid delivery to patient tissue.

As shown in FIG. 11, the method 1100 of placement of the multi-headed catheter 100 for a continuous nerve block is performed by inserting an introducer needle 300 and a sheath 350, e.g., a T-peel sheath, from a piercing site at the superior lateral aspect of the knee, just above the joint at the superior pole of the patella at step 1102. The piercing site is near, but not within, the wound site. The piercing site is sufficiently close to the wound site so that when the introducer sheath is advanced from the piercing site to the wound site, it is not snagged, blocked, or otherwise inhibited from reaching the wound site. The piercing site is sufficiently far, however, from the wound site to diminish the likelihood of infection at the wound site. The distance between the piercing site and the wound site will depend on a variety of factors, such as the type of drug used, the size of the needle/sheath assembly 370, and the size and type of the wound.

The introducer needle/T-peel sheath assembly 370 are passed under the rectus femoris tendon and into the wound site (surgical opening). In step 1104, the introducer needle 300 is then removed, leaving the T-peel sheath 350 in place. The T-peel sheath 350 forms a passage through which the multi-headed catheter 100 may be safely introduced into the wound site.

Before inserting the multi-headed catheter 100 through the T-peel sheath 350, both the first tube 110 and the second tube 120 can be flushed with saline to prevent the presence of air within either the first tube 110 or the second tube 120. The second tube 120 is inserted within the first tube 110 such that the distal end 124 of the second tube 120 is positioned within the first tube 110, as shown in FIG. 2A. Then, in step 1106, the first tube 110 is passed through the T-peel sheath 350 into the wound site and retrieved by grasping the distal end 114 of the first tube 110 to advance the multi-headed catheter 100 through the T-peel sheath 350. By using well known methods, the first tube 110 may be inserted with the aid of an axial guide wire or a stylet (not shown) positioned within the first tube 110 to stiffen the first tube 110 in order to guide the direction of the first tube 110 to aid in insertion. Alternatively, the first tube 110 can be inserted without a guide wire or stylet.

Next, in step 1108, the second tube 120 is advanced through the first tube 110 until the distal end 124 of the second tube 120 exits the opening 116 of the first tube 110. The distal end 124 of the second tube 120 can be retrieved by grasping manually, by a straight-tipped pituitary ronguer, or by any other suitable catheter placement tool and pulled through the opening 116 until a desired length of the second tube 120, including the entire perfusion section 129, extends through the opening 116. In step 1110, the distal end 124 of the second tube 120 is then advanced and positioned such that the perfusion section 129 is positioned in a desired area for a nerve block. The perfusion section 129 can be manually positioned within the open wound area or blindly positioned by blunt dissection in a deep anatomical location, e.g., by advancing the distal end 124 cephalad along the anterior surface of the medial intermuscular septum and deep to the vastus medialis oblique muscle, about 15-20 cm cephalad to the superior patella, within the adductor canal.

Then, in step 1112, the perfusion section 119 of the first tube 110 can be placed in a similar manner to that of the second tube 120. Alternatively, step 1112 of placing the perfusion section 119 of the first tube 110 can be performed before step 1110 of placing the perfusion section 129 of the second tube 120. The perfusion section 119 of the first tube 110 and the perfusion section 129 of the second tube can be placed in locations distal to each other such that the nerve block bathes a greater number of nerves affected by the TKA procedure to enable a greater reduction in post-surgical pain. For example, the perfusion section 119 of the first tube 110 can be placed in an anterior position and the perfusion section 129 of the second tube 120 can be placed in an anterior position, or vice versa. The perfusion sections 119 and 129 can be placed in any possible positions relative to the wound site so as to provide a suitable nerve block as determined by the surgeon.

After both the first tube 110 and the second tube 120 have been placed, the first tube 110 is held in place at a position proximal to the opening 116 and the T-peel sheath 350 is withdrawn by back-threading it over the first tube 110 until the distal end of the T-peel sheath 350 is fully withdrawn from the piercing site. Then, the T-peel sheath 350 is split into two portions using handles 360 and 362 or peeled away from the first tube 110 and discarded.

Next, in step 1114, the first rigid port 130 and the second rigid port 140 can be locked together using the locking tabs to form the unitary hub, with a fluid-tight seal being formed by the sealing polymer 135 to prevent any fluid from leaking out of the hub. A short length of the first tube 110 adjacent to the first rigid port 130 can be coiled, and the coil and the hub can be secured to the patient's body. For example, an adhesive strip can adhere to the patient's skin, and maintain the coil and the hub in place. In one possible embodiment, the adhesive strip includes a self-adhesive side for adhering to the patient's skin, and a hook-and-loop fastener facing away from the self-adhesive side to fasten the coil and the hub in place. Alternatively, the coil and hub can be secured with STERI-STRIPS and/or TEGADERM adhesive skin closures. Finally, in step 1116, each of the respective fluid connectors 132 and 142 can then be connected via tubing to a multi-action fluid pump 500 to deliver the nerve block drugs through the first tube 110 and the second tube 120, respectively.

Although the above-described method is an illustrative use of the multi-headed catheter 100 of the present invention, it is to be understood that the multi-headed catheter 100 may be implemented for any suitable use where a surgeon desires the use of two separate perfusion sections, or the delivery of two different drugs to a single location, or any other suitable use. For example, the multi-headed catheter 100 of the present invention can be used in other anatomical regions of the body, such as the spine, the ribs, any major joint such as the elbow, or any other area.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A multi-headed catheter comprising:
   a first tube extending along an axis and having a distal end and a proximal end, wherein the first tube has at least one exit hole provided at the distal end of the first tube to define a perfusion section of the first tube; and
   a second tube extending along the axis, wherein at least a portion of the second tube is disposed within the first tube, wherein the second tube has at least one exit hole provided at a distal end of the second tube to define a perfusion section of the second tube;
   wherein the distal end of the second tube is configured to exit the first tube at an opening provided along a wall of the first tube,
   wherein the wall of the first tube comprises an axial section located between the distal end and the proximal end, wherein the axial section is formed from a soft durometer material proximal to the distal end of the first tube and the remainder of the wall of the first tube at the proximal end and distal end is formed from a material having a firmer material than the soft durometer material of the axial section, wherein the opening of the first tube is disposed in the axial section,
   wherein the opening in the first tube is located proximal to each of the at least one exit holes of the perfusion section of the first tube.

2. The multi-headed catheter of claim 1, wherein a proximal end of the second tube is disposed within a proximal end of the first tube.

3. The mufti-headed catheter of claim 1, wherein the at least one exit hole of the first tube and/or the at least one exit hole of the second tube comprises a plurality of exit holes.

4. The multi-headed catheter of claim 1, wherein the first tube and the second tube are configured to connect with a multi-action pump to independently deliver fluid through the first tube and the second tube.

5. The multi-headed catheter of claim 1, wherein the perfusion section of the second tube is configured to exit the first tube at the opening and extend outside of the first tube.

6. The multi-headed catheter of claim 1, wherein the first tube comprises a rigid port located at a proximal end of the first tube, wherein the rigid port of the first tube is configured to connect to a pump, further wherein the second tube comprises a rigid port located at a proximal end of the second tube, wherein the rigid port of the second tube is configured to connect to the pump.

7. The multi-headed catheter of claim 6, wherein the rigid port of the first tube and the rigid port of the second tube are configured to lock together to form a hub.

8. The multi-headed catheter of claim 7, wherein the proximal end of the rigid port of the first tube comprises a locking tab, further wherein the distal end of the rigid port of the second tube comprises a locking nut configured to receive the locking tab.

9. The multi-headed catheter of claim 6, wherein the rigid port of the first tube comprises a body extending along the axis and a connector extending at an angle to the axis, wherein the connector is configured to connect to the pump.

10. The multi-headed catheter of claim 1, wherein the opening of the first tube comprises a self-sealing edge formed from the soft durometer material.

11. The multi-headed catheter of claim 1, wherein the second tube is more rigid than the first tube.

12. A fluid delivery system comprising:
    a multi-headed catheter comprising:
       a first tube extending along an axis and having a distal end and a proximal end, wherein the first tube has at least one exit hole provided at the distal end of the first tube to define a perfusion section of the first tube; and
       a second tube extending from a proximal end to a distal end along the axis, wherein at least a portion of the second tube is disposed within the first tube, wherein the second tube has at least one exit hole provided at the distal end of the second tube to define a perfusion section of the second tube;
       wherein the distal end of the second tube is configured to exit the first tube at an opening provided along a wall of the first tube,
       wherein the wall of the first tube comprises an axial section located between the distal end and the proximal end, wherein the axial section is formed from a soft durometer material proximal to the distal end of the first tube and the remainder of the wall of the first tube at the proximal end and distal end is formed from a material having a firmer material than the soft durometer material of the axial section, wherein the opening of the first tube is disposed in the axial section; and
    a multi-action fluid pump configured to independently deliver fluid from the proximal end of the first tube through the at least one exit hole of the first tube and from the proximal end of the second tube through the at least one exit hole of the second tube.

13. The fluid delivery system of claim 12, wherein the first tube is configured to be inserted into an anatomical region of a patient.

14. The fluid delivery system of claim 12, wherein the second tube is configured to be inserted through a proximal end of the first tube.

15. The fluid delivery system of claim 12, wherein the distal end of the second tube is configured to be located within the first tube during insertion of the first tube into an anatomical region of a patient.

16. The fluid delivery system of claim 12, wherein the distal end of the second tube is configured to be pulled through the opening of the first tube after insertion and manually positioned at an anatomical location within a patient's body.

17. The fluid delivery system of claim 12, further comprising an introducer comprising a tube configured to receive the first tube of the multi-headed catheter.

18. The fluid delivery system of claim 12, wherein the multi-action fluid pump is configured to deliver fluid through the first tube at a first flow rate and to the second tube at a second flow rate.

19. The fluid delivery system of claim 18, wherein the first flow rate and the second flow rate are not equal.

20. A method of performing a nerve block, the method comprising steps of:
- providing a multi-headed catheter comprising: a first tube extending along an axis and having a distal end and a proximal end, wherein the first tube has at least one exit hole provided at the distal end of the first tube to define a perfusion section of the first tube; and a second tube extending along the axis, wherein at least a portion of the second tube is disposed within the first tube, wherein the second tube has at least one exit hole provided at a distal end of the second tube to define a perfusion section of the second tube; wherein the distal end of the second tube is configured to exit the first tube at an opening provided along a wall of the first tube, wherein the opening in the first tube is located proximal to each of the at least one exit holes of the perfusion section of the first tube, wherein the wall of the first tube comprises an axial section located between the distal end and the proximal end, wherein the axial section is formed from a soft durometer material proximal to the distal end of the first tube and the remainder of the wall of the first tube at the proximal end and distal end is formed from a material having a firmer material than the soft durometer material of the axial section, wherein the opening of the first tube is disposed in the axial section;
- providing a multi-action fluid infusion pump, the pump comprising a first tubing and a second tubing;
- inserting an introducer through the skin of a patient adjacent an open surgical wound site of the patient;
- advancing the introducer needle to the open surgical area;
- threading the first tube of the multi-headed catheter through the introducer to the open surgical wound site of the patient;
- pulling the second tube of the multi-headed catheter through the opening of the first tube of the multi-headed catheter;
- positioning the perfusion section of the second tube at a second location within the patient's body accessed by the open surgical wound site;
- positioning the perfusion section of the first tube at a first location within the patient's body accessed by the open surgical wound site;
- withdrawing the introducer from the patient then removing the introducer away from the first tube;
- connecting the first tubing of the pump to the first tube of the multi-headed catheter and connecting the second tubing of the pump to the second tube of the multi-headed catheter; and
- independently delivering fluid from the pump through the first tubing and the second tubing to the first location and the second location, respectively.

21. The method of claim 20, wherein the first tube comprises a rigid port located at a proximal end of the first tube, wherein the rigid port of the first tube is configured to connect to a pump, further wherein the second tube comprises a rigid port located at a proximal end of the second tube, wherein the rigid port of the second tube is configured to connect to the pump;
- further comprising a step of locking the first rigid port to the second rigid port to form a unitary hub having a fluid-tight seal.

* * * * *